(12) United States Patent
Fung

(10) Patent No.: US 8,029,456 B2
(45) Date of Patent: Oct. 4, 2011

(54) COMPACT INTRAVAGINAL DEVICE APPLICATOR

(75) Inventor: Paul Y. Fung, South River, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 557 days.

(21) Appl. No.: 12/059,451

(22) Filed: Mar. 31, 2008

(65) Prior Publication Data

US 2009/0247930 A1    Oct. 1, 2009

(51) Int. Cl.
*A61F 13/20* (2006.01)

(52) U.S. Cl. .......................... 604/15; 604/904

(58) Field of Classification Search ............ 604/385.17, 604/385.18, 904, 11–18
See application file for complete search history.

(56) References Cited

U.S. PATENT DOCUMENTS

| | | |
|---|---|---|
| 2,832,342 A | 4/1958 | Wingenroth |
| 3,090,385 A | 5/1963 | Brecht |
| 4,269,187 A | 5/1981 | Sakurai et al. |
| 4,273,125 A | 6/1981 | Sakurai |
| 4,276,881 A | 7/1981 | Lilaonitkul |
| 4,286,595 A | 9/1981 | Ring |
| 4,329,991 A | 5/1982 | Sakurai |
| 4,332,251 A | 6/1982 | Thompson |
| 4,498,899 A | 2/1985 | Gross |
| 4,676,773 A * | 6/1987 | Sheldon ................... 604/16 |
| 4,699,610 A | 10/1987 | Hanano et al. |
| 4,726,805 A | 2/1988 | Sanders, III |
| 4,857,044 A | 8/1989 | Lennon |
| 4,891,042 A | 1/1990 | Melvin et al. |
| 4,911,687 A | 3/1990 | Stewart et al. |
| 4,921,474 A | 5/1990 | Suzuki et al. |
| 4,960,417 A | 10/1990 | Tarr, Jr. et al. |
| 4,973,302 A | 11/1990 | Armour et al. |
| 5,080,659 A | 1/1992 | Nakanishi |
| 5,330,421 A | 7/1994 | Tarr et al. |
| 5,554,109 A | 9/1996 | Frayman |
| 5,599,293 A | 2/1997 | Orenga et al. |
| 5,643,196 A | 7/1997 | Child et al. |
| 5,750,446 A | 5/1998 | Nguyen et al. |
| 6,019,744 A | 2/2000 | Altdorf et al. |
| 6,840,927 B2 | 1/2005 | Hasse et al. |
| 7,320,673 B2 | 1/2008 | Gann et al. |
| 2002/0111578 A1* | 8/2002 | Buzot ..................... 604/14 |
| 2004/0199102 A1 | 10/2004 | LeMay et al. |

FOREIGN PATENT DOCUMENTS

| | | |
|---|---|---|
| EP | 606923 A | 7/1994 |
| WO | WO 90/11747 A | 10/1990 |
| WO | WO 02/076182 A | 10/2002 |

\* cited by examiner

*Primary Examiner* — Michele M Kidwell

(57) ABSTRACT

The present invention provides a compact intravaginal device applicator assembly having a longitudinal axis comprises an elongated barrel with an insertion end and an opposite gripper end; an intravaginal device and a plunger with a restraint.

10 Claims, 5 Drawing Sheets

COMPACT INTRAVAGINAL DEVICE APPLICATOR

FIELD OF THE INVENTION

The present invention relates to an applicator for delivering intravaginal devices into the body and in particular to a compact applicator having a plunger and insertion barrel.

BACKGROUND OF THE INVENTION

Women use intravaginal devices for a variety of reasons. The most common device is a catamenial tampon used for the retention of fluid or menses discharged during the menstrual cycle. Other intravaginal devices may include urinary incontinence devices, collection cups, birth control devices, and inflation devices. These various devices can be used to block menstrual fluid, supply medicaments to the vagina, facilitate normal function, assist in the recovery and restoration of tissues and organs that have deteriorated from traumatic or systemic changes, injury or infection, and enhance the tone, health or function of the vagina, cervix and related organs, and tissues through biological, chemical and/or physical action.

Intravaginal devices can be inserted into the body by either digital insertion or by use of an applicator. The prior art is replete with examples of applicators, especially for tampons. For example, there are applicators made of cardboard or molded thermoplastic material. Some applicators flushable and some have insertion ends that have a "closed" configuration due to the use of molded petals. Regardless of the materials and insertion designs, most applicators have two parts: an insertion member or barrel and a plunger.

As with any feminine hygiene article or intravaginal device, discretion and portability are important. Women often carry around these devices in their purses and do not expect the devices to be noticeable.

Conventional tampon applicators are sold in which the tampon is located within the barrel and the plunger extended outwardly. Upon use, the plunger is pushed into the barrel, expelling the tampon out the insertion end of the barrel. Compact applicators are much shorter than conventional applicators. The compact applicator may contain the tampon and plunger within the barrel. Prior to use, the plunger is normally withdrawn out the withdrawal end of the barrel. Once the plunger engages the withdrawal end of the tampon, the applicator is inserted into the body and pressure is applied to the plunger to expel the tampon out the insertion end of the barrel. One example of a compact applicator can be seen in U.S. Pat. No. 4,676,773. In this patent, the applicator provides a plunger, which is nested within the outer insertion tube. The plunger has slits on the leading edge to receive the tampon and a ring positioned around the trailing end. The tampon is expelled when the plunger is pulled backward by the inwardly compressive forces provided by the ring.

Difficulties encountered in making and using a compact applicator revolve around the plunger completely disengaging from the barrel, the plunger not contacting the withdrawal end of the tampon, the plunger not having sufficient column strength to expel the tampon, etc. For these reasons, there exists a need for a compact applicator that is discrete, easy to use, and reliable.

SUMMARY OF THE INVENTION

The present invention provides a compact intravaginal device applicator assembly having a longitudinal axis comprising an elongated barrel with an insertion end and an opposite gripper end; an intravaginal device and a plunger with a restraint.

The barrel of the compact applicator is elongated having an insertion end configured to provide a first opening and an opposite gripper end, the gripper end has a second opening that is smaller than the first opening.

Intravaginal devices have a major dimension perpendicular to the longitudinal axis of the assembly that is greater than a corresponding dimension of the second opening.

The plunger is slidably positioned within the barrel and comprises a hollow tube having a first end contained within the barrel and a second end, opposite the first, extending through the second opening of the barrel and having slits extending from the first end and terminating a distance spaced from a second end, to form a plurality of flaps having side edges defined by the slits, a restraint attached proximate to the first end of the tube, arranged and configured to separate the flaps to accommodate the intravaginal device within the barrel.

DETAILED DESCRIPTION OF THE INVENTION

Figure 1A:
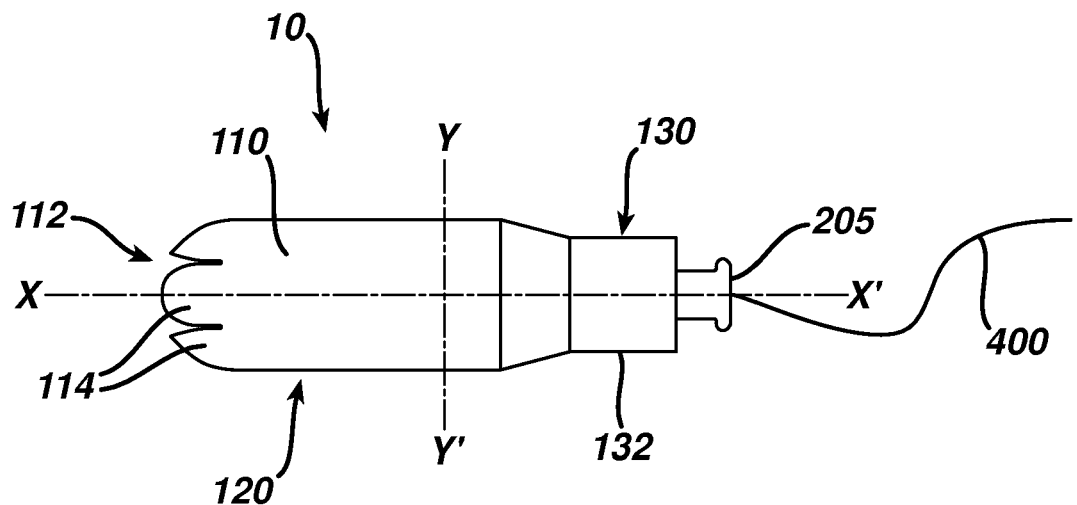
FIG. 1A is a side elevation of an intravaginal device applicator assembly of the present invention
Figure 1B:
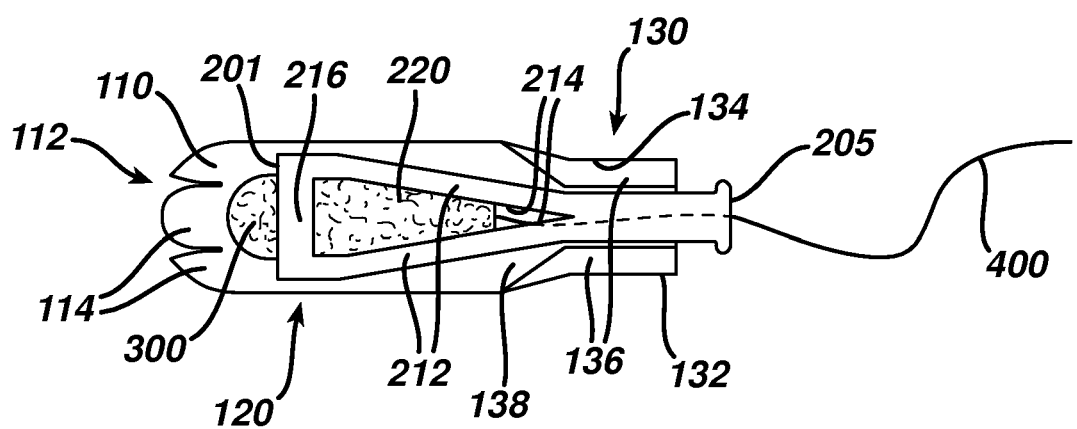
FIG. 1B is a longitudinal cross-section of the applicator barrel of FIG. 1A with a side elevation of the applicator plunger and tampon pledget contained therein.

The present invention is generally directed to a compact applicator for inserting intravaginal devices within the human body. In general, the compact applicator of the present invention shall have two portions, the barrel, and plunger. The applicator has a longitudinal axis X-X' as shown in FIG. 1. As used herein, the term "barrel" shall mean that portion of the applicator that is inserted into the body. The barrel can hold intravaginal device and has two ends, an insertion end, and a finger grip (gripper or withdrawal) end. The insertion end may be opened or may be in a closed configuration by the use of petals commonly known in the art. At the gripper end there may be a finger grip. As used herein, the term "plunger" shall mean that portion of the applicator that actually pushes the tampon out of the barrel. The plunger is slideably positioned within the barrel.

As used herein, the term "intravaginal device" may be any device that is inserted into the vaginal canal. Examples of intravaginal devices include conventional tampons, urinary incontinence devices, birth control devices, inflation devices or blocking devices, or menstrual cups and devices that are designed to supply medicaments to the vagina or facilitate normal function or to assist in the recovery and restoration of tissues and organs that have deteriorated from traumatic or systemic changes, injury or infection.

Figure 4:
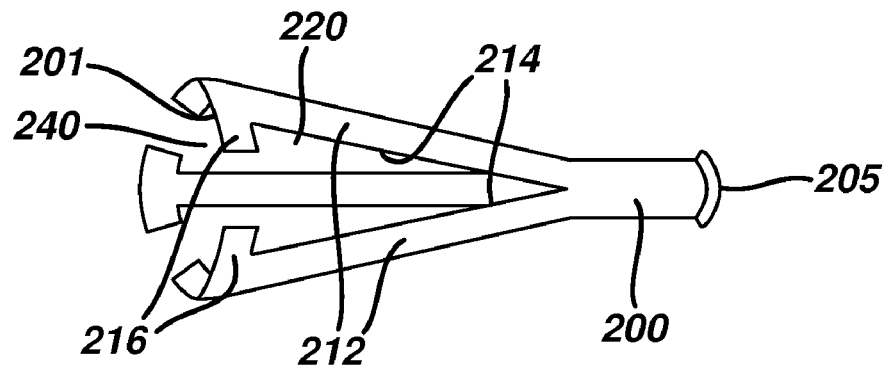
FIG. 4 is a perspective view of an alternative embodiment of a plunger according to the present invention.
Figure 5:
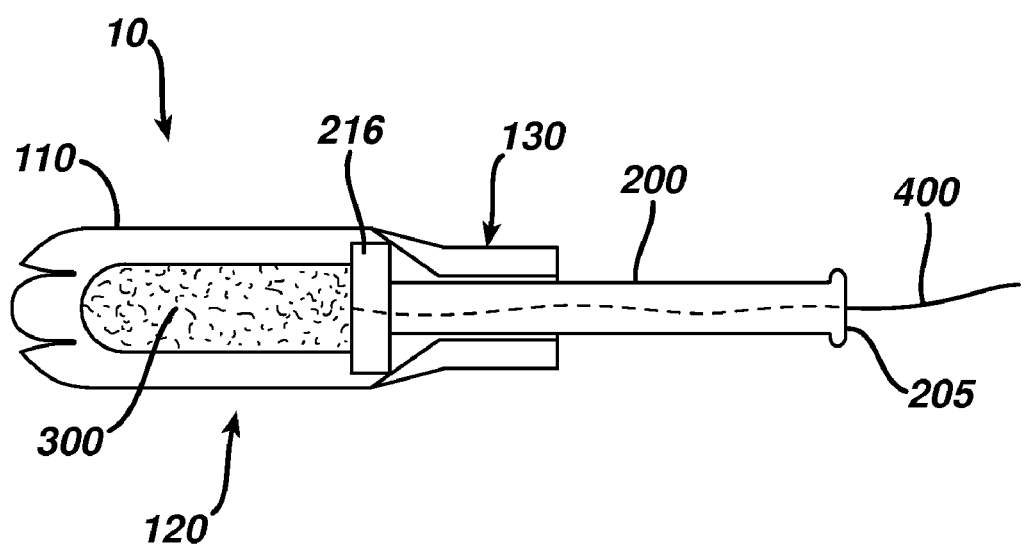
FIG. 5 is the cross-section and side elevation view of FIG. 1B with the plunger having been withdrawn from around the tampon.

Turning to the Figures, the compact applicator assembly can be seen from FIG. 1-13. A compact tampon applicator assembly 10 as seen in FIG. 1 has two portions, an elongate barrel 100 and plunger 200. The barrel 100 and plunger 200 are aligned such that the compact applicator has a longitudinal axis X-X' and lateral axis Y-Y'. The barrel 100 possesses a main body 120 with the inner surface and the outer surface; a finger grip portion 130 with the inner surface 134 and the outer surface 132, an insertion end 110 configured to provide a first opening 114 and an opposite gripper end 130, wherein the gripper end 130 has a second opening 138 that is smaller than the first opening 114. As seen in FIGS. 1, 5 and 13, plunger 200 is slidably positioned within the barrel 100. As shown in FIG. 1, tampon 300 can be contained within plunger 200. As shown in FIG. 1, plunger 200 extends through the second opening 138 of gripper end 130 of the barrel 100.

The applicator will now be discussed in further detail.

Barrel

The barrel of the present invention is similar to those known in the art. The barrel 100 has an insertion end 100 and a gripper end 130. The finger grip portion 130 of barrel 100 has a dimension that is smaller than the dimension of the insertion end 110 and main body of the barrel 120. This smaller dimension may help align the plunger as it is withdrawn from the barrel and as it is pushed back into the barrel upon deploying or expelling the tampon. The smaller finger grip also allows the user to firmly grip the applicator and also aids in placement of the tampon.

Typically a barrel has a total length of 65-85 mm and diameter of 12-17 mm, more preferably a length of 75 mm and diameter of 15 mm. Finger grip portion of the barrel has a length of 14-18 mm and diameter of 13-16 mm, more preferably a length of 16 mm and diameter of 13 mm. The inner surface of the gripper end of the barrel may have one to five ribs along the longitudinal axis of the assembly, more preferably three ribs and most preferably one rib. The rib may have length (height) of about 10 to 16 mm and width of 1 to 3 mm, more preferably length of 10 mm and width of 2 mm, and most preferably length of 12 mm and width of 1.5 mm. The ribs helps keep the plunger aligned during withdrawal and ejection of the tampon. During the ejection process of intravaginal devices, the rib located at the inner surface of the gripping end of the barrel prevents the removal of the outwardly collapsed restraint through the gripper end of the barrel, and thus helps the plunger to remain inside the barrel and to facilitate the smooth insertion of the intravaginal device.

Figure 11:
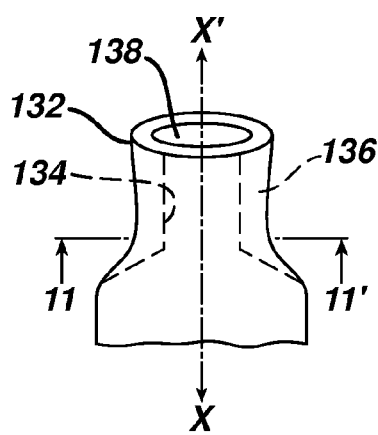
FIG. 11 is a partial perspective view of a hollow finger grip portion of the barrel, showing the position of the wall at the inner surface of the barrel of the finger grip portion.
Figure 12:
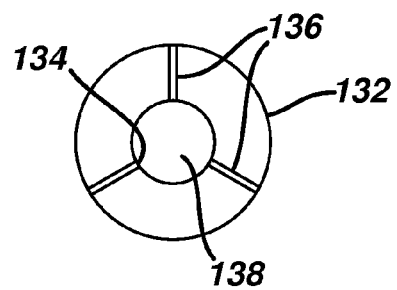
FIG. 12 is a cross-section of the finger grip portion of the barrel taken along line 11-11' of FIG. 11.
Figure 13:
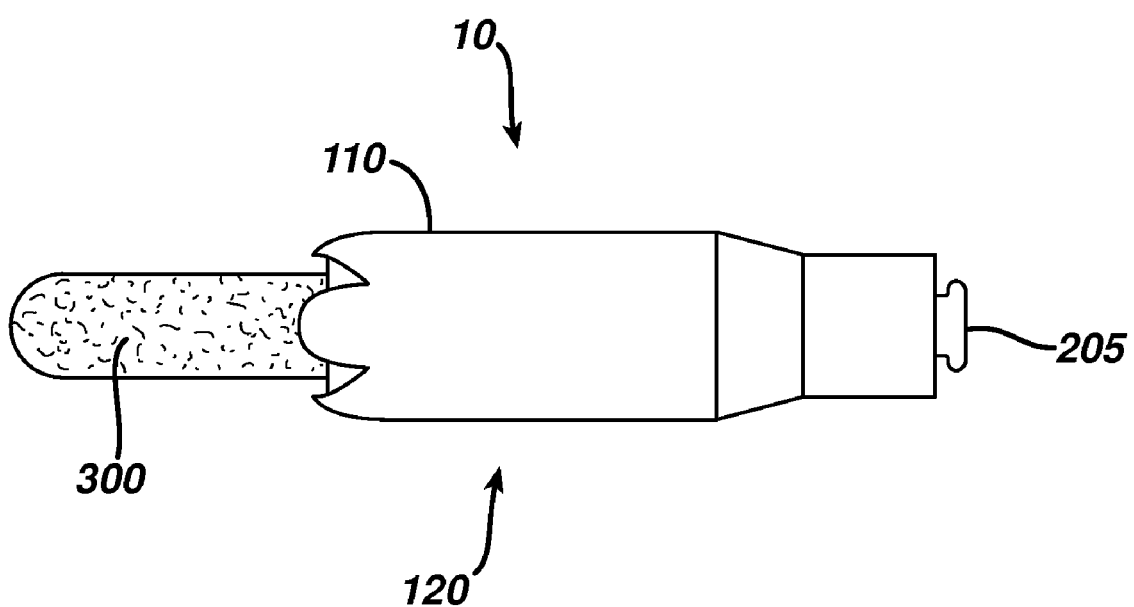
FIG. 13 is the cross-section and side elevation view of FIG. 1B with the plunger ejecting the tampon pledget from the applicator.

FIGS. 11 and 12 shows the inner surface of the finger grip portion 134 of the applicator possesses three ribs 136 along the longitudinal axis X-X' of the assembly 10.

The insertion end 110 may be open such that the tampon is visible from the opening while still contained within the barrel. Alternatively, the insertion end may have a series of petals are formed and molded into a domed shape. In the later configuration, the tampon is not visible from the opening. This configuration allows for a smooth insertion but may require additional force when expelling the tampon from the applicator.

Plunger

Figure 3:
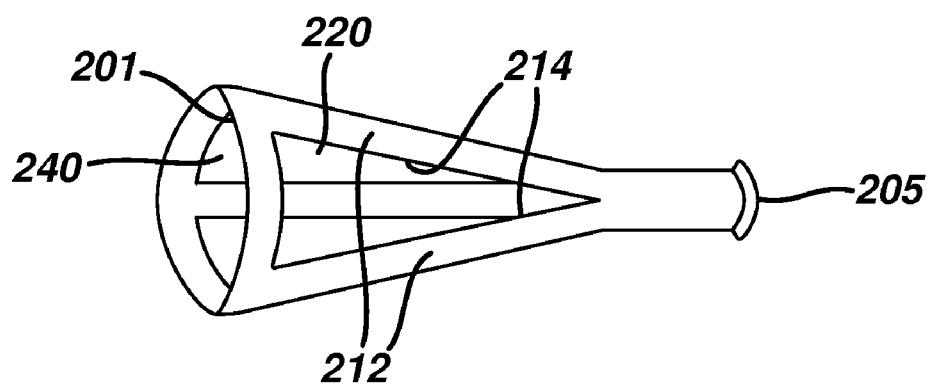
FIG. 3 is a perspective view of the plunger of FIG. 2.

Plunger 200 is a hollow tube having a first end 201 and a second end 205, opposite the first end 201. Plunger 200 as shown in FIGS. 3 and 4, has flaps 212, which surround chamber 240 formed within the hollow tube. The plunger further possesses a restraint attached proximate to the first end of the tube. The restraint is arranged and configured to separate the flaps in order to accommodate the tampon or intravaginal device within the barrel.

As shown in the figures, first end 201 of plunger 200 has at least one restraint 216, which bridges the gap between flaps 212. In one embodiment the restraint 216 is continuous around the tampon. In another embodiment, the restraint is discontinuous.

Figure 6:
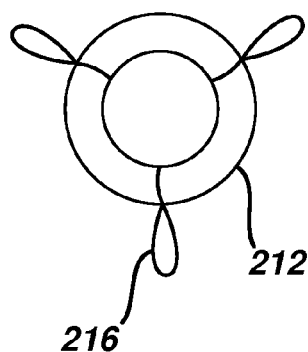
FIG. 6 is a lateral cross-section of a plunger of the present invention showing an interlocking configuration.
Figure 7:
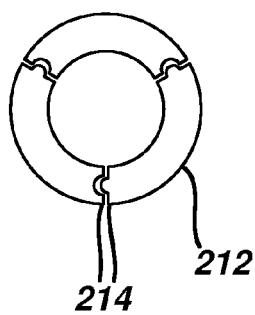
FIGS. 7 and 8 are lateral cross-sections of alternative embodiments of plungers of the present invention.
Figure 8:
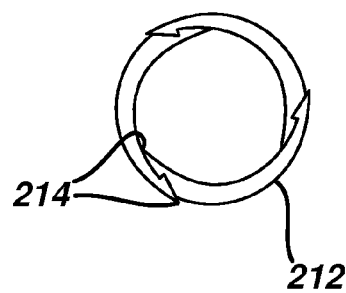
Figure 9:
FIG. 9 is a detailed view of a portion of FIG. 7.
Figure 10:
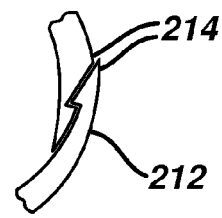
FIG. 10 is a detailed view of a portion of FIG. 8.

The plunger has two configurations, a first configuration when the flaps of the plunger are separated from each other and connected with the restraint in order to accommodate the intravaginal device within the chamber of the plunger and a second configuration after the tampon has been expelled from the chamber such that the flaps of the plunger are interlocked to form a closed hollow cylindrical tube during the ejection of the said intravaginal device. In one embodiment shown in FIGS. 1-3, 6, the restraint is a flexible material that forms a ring and surrounds the tampon in the first configuration. In the second configuration, the flaps as seen in FIG. 6, are in abutting relationship. The restraints are loosely folded outward. The surface formed by the flaps and restraints contacts the withdrawal end of the tampon. It is this surface that causes the tampon to be expelled from the barrel.

As seen in FIGS. 3 and 4, plunger 200 further have at least one side opening 220 extending from the first end 201 and terminating a distance spaced from a second end 205, to form at least one flap 212 having side edges 214. In one embodiment, there is one side opening and one flap. In another embodiment, there are two side openings and two flaps. In another embodiment, there are three side openings and three flaps. The number will be dependent upon the size of the barrel and plunger and the force required to expel the tampon. A plunger having a large number of side openings may have flaps, which are weak due to their number.

In one embodiment shown in FIG. 3, restraint member 216 is continuous. When a tampon is contained within the chamber 240, restraints 216 form a ring around the insertion end of the tampon.

If the restraint 216 is discontinuous as shown in FIG. 4, the tampon will still be secured within the chamber 240 but the restraints will not be connected.

Further examples of the restraint member in a deployed state can be seen in FIG. 5-10. As shown, the side edges 214 of the flaps 212 interlock with the side edge of the adjacent flap. Some ways to interlock the side edges 214 include but are not limited to tongue and groove (FIGS. 7, 9) or Zip lock or Hook lock (FIGS. 8, 10) or by combination thereof. Additionally, FIGS. 1-3, 6 show a restraint member that may have flexible or elastic capabilities.

Figure 2:
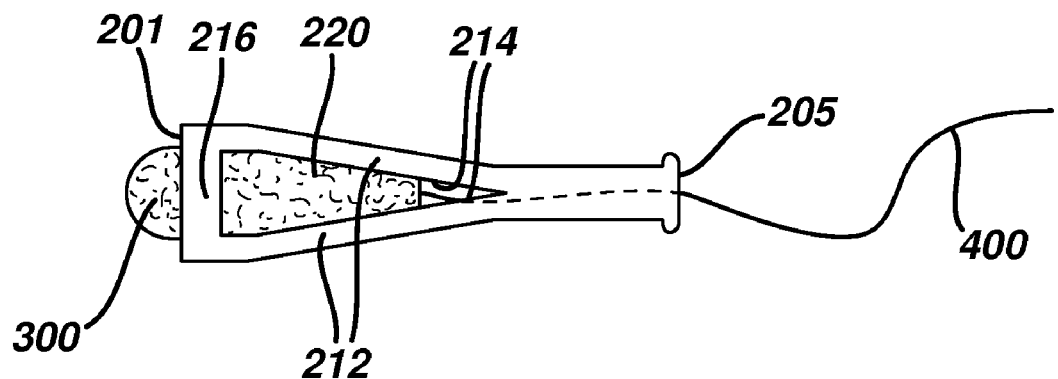
FIG. 2 is a side elevation of the plunger of the intravaginal device applicator of FIGS. 1A-B and showing accommodation of tampon in the plunger.

As seen in FIGS. 2 and 3, restraint 216 is attached proximate to the first end 201 of the tube, arranged and configured to separate the flaps 212 to accommodate a tampon pledget 300 within the barrel 100.

Upon use, the plunger is withdrawn through the gripper end of the barrel. As the plunger moves through the narrow opening, the tampon is forced out of the chamber 240, remaining in the barrel. Additionally, as this is happening, the flaps of the first end 200 of the plunger move and are held together by the narrowing of the barrel gripper end. The first end 201 of the plunger now contacts the withdrawal end of the tampon.

In one embodiment, the restraint of the present invention is made of a ring that has a major dimension perpendicular to the longitudinal axis of the assembly that is greater than the diameter of the intravaginal device. The ring has flap portions associated with the flaps and connecting portions connecting adjacent flap portions. The ring exhibits at least two stable configurations; a first, large diameter configuration to support the plunger flaps when containing the intravaginal device and a second collapsed configuration when the side edges of the plunger flaps contact each other and the connecting portions of the ring are displaced outwardly to prevent removal of the restraint through the second opening of the barrel.

The restraint may advantageously be attached proximate to the first end of the tube, so as to provide sufficient opening to fully accommodate intravaginal device within the barrel during the initial or packaging stage or before use.

The restraint of the present invention can be made of plastic or elastic or rubber or extensible material or of the same material that of plunger or barrel is made of.

According to another advantageous embodiment, the restraint material preferably has a low coefficient of friction, contacting face of the said restraint (both exterior and interior) optionally coated with a lubricating substance, to help the smooth frictionless movement of plunger during the use.

The restraint of the present invention allows the flaps of the plunger to remain flexible and connected with the adjacent flap of the plunger. Moreover, the restraint could be extensible and stretchable more than 60-90% of the original dimensions.

During the ejection process of the intravaginal device, the flaps of the plunger contact with the adjacent side edges of the flaps of the plunger and attain a stable interlocked configuration.

In one embodiment of the invention interlocking of the flaps of the plunger is attained by having tongue and groove configuration wherein the one side edge of the flap have a raised portion like a tongue which articulates with the adjacent side edge of the flaps having a depressed portion.

Both the barrel and plunger can be made of plastic, biodegradable material or cardboard. In particular, plastic materials such as polyethylene, polypropylene, polyurethane, polyesters, ethylene-vinyl acetate, polystyrene or poly vinyl chloride (PVC) can be used to form the applicator of the invention. Biodegradable materials which can be used to form the applicator of the invention are for example described in EP 0 606 923 A1.

Tampon

In one embodiment, the compact applicator of the present invention contains a tampon. As shown in the figures, compact applicator 10 contains a cylindrical tampon 300 with a removal string 400. The tampon 300 has a greater dimension than the corresponding dimension of the second or gripper opening 138 of the barrel 100.

The intravaginal device comprises an outer perimeter, an insertion end, and a withdrawal end opposed to the insertion end. The intravaginal devices have major dimension perpendicular to the longitudinal axis of the assembly that is greater than a corresponding dimension of the second opening of the barrel.

In one embodiment the intravaginal device is a tampon. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis, and a radial axis. The tampon's length can be measured from the insertion end to the withdrawal end along the longitudinal axis. A typical compressed tampon for human use is 30-60 mm in length. A tampon may be straight or non-linear in shape, such as curved along the longitudinal axis. A typical compressed tampon is 8-20 mm wide. The width of a tampon, unless otherwise stated in the specification, corresponds to the length across the largest cylindrical cross-section, along the length of the tampon. As used herein "mm" is millimeters.

In this invention, the user can use the compact applicator to deliver an intravaginal device. The intravaginal device is contained in a compact applicator assembly having a longitudinal axis. The applicator assembly has an elongate barrel with an insertion end configured to provide a first opening and an opposite gripper end. The gripper end of the barrel has a second opening that is smaller than the first opening. The intravaginal device has a major dimension perpendicular to the longitudinal axis of the assembly that is greater than a corresponding dimension of the second opening. The compact applicator also has a plunger that is slidably positioned within the barrel and is a hollow tube that has a first end contained within the barrel. The second end of the plunger, which is opposite the first end, extends through the second opening of the barrel. The plunger has side openings that extend from the first end and terminate a distance spaced from a second end. These side openings form a plurality of flaps having side edges, which are defined by the side openings. The plunger also has a restraint attached proximate to the first end of the tube, arranged, and configured to separate the flaps to accommodate the intravaginal device within the barrel. During insertion of the intravaginal device, the user would withdraw a majority of the plunger from the barrel by sliding the plunger through the second opening such that the plunger takes the form of a substantially closed cylindrical tube with the adjacent side edges of the flaps contacting each other and collapsing the restraint. The user would slide the plunger into the barrel through the second opening to urge the restraint against an end of the intravaginal device and force the intravaginal device out of the first opening.

I claim:

1. A compact intravaginal device applicator assembly having a longitudinal axis comprising;
   a) an elongate barrel having an insertion end configured to provide a first opening and an opposite gripper end, wherein the gripper end has a second opening that is smaller than the first opening;
   b) an intravaginal device having a major dimension perpendicular to the longitudinal axis of the assembly that is greater than a corresponding dimension of the second opening;
   c) a plunger that is slidably positioned within the barrel and that comprises:
      i) a hollow tube having a first end contained within the barrel and a second end, opposite the first, extending through the second opening of the barrel and having slits extending from the first end and terminating a distance spaced from a second end, to form a plurality of flaps having side edges defined by the slits,
      ii) a restraint attached proximate to the first end of the tube, arranged and configured to separate the flaps to accommodate the intravaginal device within the barrel.

2. The compact applicator of claim 1, wherein the flaps of the plunger are arranged and configured to articulate from a first state, separated from adjacent flaps to accommodate the intravaginal device within the barrel, and a second state, forming a substantially closed cylindrical tube wherein adjacent side edges of the flaps contact each other.

3. The compact applicator of claim 2, wherein the restraint comprises a ring having a major dimension perpendicular to the longitudinal axis of the assembly that is greater than the diameter of the intravaginal device; wherein the ring comprises (1) flap portions associated with the flaps and (2) connecting portions connecting adjacent flap portions; and wherein the ring exhibits at least two stable configurations; a first, large diameter configuration to support the plunger flaps when containing the intravaginal device, a second collapsed configuration when the side edges of the plunger flaps contact each other and the connecting portions of the ring are displaced outwardly to prevent removal of the restraint through the second opening.

4. The compact applicator of claim 1, wherein an inner surface of the said barrel at finger grip portion comprises at least one rib to prevent removal of the restraint through the second opening.

5. The compact applicator of claim 1 wherein at least one of the barrel and the plunger comprise a polymeric material.

6. A compact tampon applicator assembly having a longitudinal axis comprising;
 a) an elongate barrel having an insertion end configured to provide a first opening and an opposite gripper end, wherein the gripper end has a second opening that is smaller than the first opening;
 b) a generally cylindrical tampon pledget having a major dimension perpendicular to the longitudinal axis of the assembly that is greater than a corresponding dimension of the second opening;
 c) a plunger that is slidably positioned within the barrel and that comprises:
  i) a hollow tube having a first end contained within the barrel and a second end, opposite the first, extending through the second opening of the barrel and having slits extending from the first end and terminating a distance spaced from a second end, to form a plurality of flaps having side edges, each of said side edges comprising means to interlock an adjacent side edge,
  ii) a restraint attached proximate to the first end of the tube, arranged and configured to separate the flaps to accommodate a tampon pledget within the barrel.

7. The compact tampon applicator of claim 6, wherein the means to interlock the adjacent side edges is selected from the group consisting of tongue and groove, zip lock, hook lock, and combinations thereof.

8. The compact tampon applicator of claim 6, wherein the flaps of the plunger are capable of movement to form a substantially closed cylindrical tube wherein adjacent side edges of the flaps interlock with each other.

9. A method of ejecting an intravaginal device from a compact applicator assembly having a longitudinal axis the assembly comprising;
 a) an elongate barrel having an insertion end configured to provide a first opening and an opposite gripper end, wherein the gripper end has a second opening that is smaller than the first opening;
 b) an intravaginal device having a major dimension perpendicular to the longitudinal axis of the assembly that is greater than a corresponding dimension of the second opening;
 c) a plunger that is slidably positioned within the barrel and that comprises:
  i) a hollow tube having a first end contained within the barrel and a second end, opposite the first, extending through the second opening of the barrel and having slits extending from the first end and terminating a distance spaced from a second end, to form a plurality of flaps having side edges defined by the slits,
  ii) a restraint attached proximate to the first end of the tube, arranged and configured to separate the flaps to accommodate the intravaginal device within the barrel;
the method comprising the steps of:
(1) withdrawing a majority of the plunger from the barrel by sliding the plunger through the second opening; wherein the plunger takes the form of a substantially closed cylindrical tube wherein adjacent side edges of the flaps contact each other;
(2) collapsing the restraint;
(3) sliding the plunger into the barrel through the second opening to urge the restraint against an end of the intravaginal device and forcing the intravaginal device out of the first opening.

10. The method of claim 9, further comprising the step of interlocking adjacent side edges of adjacent flaps.

\* \* \* \* \*